United States Patent
Kawaguchi et al.

(10) Patent No.: US 11,911,420 B2
(45) Date of Patent: Feb. 27, 2024

(54) **PROPHYLACTIC AND/OR THERAPEUTIC AGENTS FOR *STREPTOCOCCUS PNEUMONIAE* INFECTION**

(71) Applicant: Nutri Co., Ltd., Yokkaichi (JP)

(72) Inventors: Susumu Kawaguchi, Yokkaichi (JP); Miho Kato, Yokkaichi (JP)

(73) Assignee: NUTRI CO., LTD., Yokkaichi (JP)

( * ) Notice: Subject to any disclaimer, the term of this patent is extended or adjusted under 35 U.S.C. 154(b) by 6 days.

(21) Appl. No.: 16/962,921

(22) PCT Filed: Jan. 31, 2019

(86) PCT No.: PCT/JP2019/003296
§ 371 (c)(1),
(2) Date: Jul. 17, 2020

(87) PCT Pub. No.: WO2019/151371
PCT Pub. Date: Aug. 8, 2019

(65) Prior Publication Data
US 2021/0379124 A1 Dec. 9, 2021

(30) Foreign Application Priority Data
Jan. 31, 2018 (JP) .................................. 2018-015333

(51) Int. Cl.
*A61K 35/744* (2015.01)
*A61P 31/04* (2006.01)

(52) U.S. Cl.
CPC ............ *A61K 35/744* (2013.01); *A61P 31/04* (2018.01)

(58) Field of Classification Search
CPC .............................. A61K 35/744; A61P 31/04
See application file for complete search history.

(56) References Cited

U.S. PATENT DOCUMENTS

| | | | |
|---|---|---|---|
| 9,492,487 B2 * | 11/2016 | Garner | ................... A61K 35/74 |
| 2009/0285920 A1 | 11/2009 | Lee et al. | |
| 2009/0297482 A1 | 12/2009 | Dicks et al. | |

FOREIGN PATENT DOCUMENTS

| | | |
|---|---|---|
| EP | 1816190 A1 | 8/2007 |
| JP | 2002-179580 A | 6/2002 |
| JP | 2003-040785 A | 2/2003 |
| JP | 2003-137795 A | 5/2003 |
| JP | 2003-261453 A | 9/2003 |
| JP | 2009-538614 A | 11/2009 |
| JP | 2013-056851 A | 3/2013 |
| JP | 2014-517003 A | 7/2014 |
| JP | 2017-001961 A | 1/2017 |

OTHER PUBLICATIONS

International Search Report issued in corresponding International Patent Application No. PCT/JP2019/003296 dated Apr. 23, 2019.
Extended European Search Report issued in corresponding European Patent Application No. 19748316.7 dated Sep. 17, 2021.
Kawakami, "Pathogenesis of Pneumococcal Infection and Immunity Mechanism of Vaccines", Journal of the Japanese Society of Internal Medicine, 2015, 104(11), pp. 2307-2313.
Journal of the Japanese Society of Internal Medicine, 2015, 104(11), pp. 2307-2313.
Office Action dated Jan. 11, 2023, issued in corresponding Japanese Patent Application No. 2019-569207.

* cited by examiner

*Primary Examiner* — Robert A Zeman
(74) *Attorney, Agent, or Firm* — Morgan, Lewis & Bockius LLP

(57) ABSTRACT

Provide is a novel prophylactic and/or therapeutic agent for *Streptococcus pneumoniae* infection. It was found that a bacterium belonging to the genus *Enterococcus* can prevent and/or treat *Streptococcus pneumoniae* infection. The prophylactic and/or therapeutic agent for *Streptococcus pneumoniae* infection, comprises a bacterium belonging to the genus *Enterococcus*. Also provided are: a medicine for prevention and/or treatment of *Streptococcus pneumoniae* infection, comprising a bacterium belonging to the genus *Enterococcus*; and a food for prevention and/or treatment of *Streptococcus pneumoniae* infection, comprising a bacterium belonging to the genus *Enterococcus*.

11 Claims, 6 Drawing Sheets

PROPHYLACTIC AND/OR THERAPEUTIC AGENTS FOR *STREPTOCOCCUS PNEUMONIAE* INFECTION

TECHNICAL FIELD

The present invention relates to agents for prevention and/or treatment of *Streptococcus pneumoniae* infection.

BACKGROUND ART

*Streptococcus pneumoniae* is a Gram-positive diplococcus that is known as an indigenous bacterium in upper respiratory tract. It is a major causative pathogen of respiratory diseases.

The National Institute of Infectious Diseases reports that *Streptococcus pneumoniae* is the most common pathogenic microorganism in community-acquired pneumonia (CAP) (Non-Patent Document 1), that in their prospective study of CAP and health-care-associated pneumonia (NHCAP), the frequency of *Streptococcus pneumoniae* was the highest (34.8% and 33.9%, respectively) (Non-Patent Document 2), and that the risk of bacteremia in patients presenting with chills and shaking was 12.1 times higher (95% confidence interval [CI] 4.1-36.2) than that in patients without them (Non-Patent Document 3). As well as for administration of appropriate antimicrobial agents, public subsidies have been provided in Japan since Oct. 1, 2014 for regular administration of *Streptococcus pneumoniae* vaccine to elderly patients aged 65 years or older.

However, the existence of antimicrobial resistant *Streptococcus pneumoniae* bacteria was confirmed. There are some reports that vaccination has not been practiced to a required extent. For these reasons, a new countermeasure is desired.

CITATION LIST

Non Patent Literature

[Non-patent Document 1].
Bartlett J G, et al., N Engl J Med 333: 1618, 1995
[Non-patent Document 2].
Fukuyama H, et al., Published online J Infect Chemother, 25 Jan. 2013
[Non-patent Document 3].
Tokuda Y, et al., Am J Med 118(12): 1417, 2005

SUMMARY OF INVENTION

Technical Problem

It is an object of the present invention to provide novel agents for prevention and/or treatment of *Streptococcus pneumoniae* infection.

Solution to Problem

As a result of intensive efforts, the inventors have found that a lactic acid bacterium belonging to the genus *Enterococcus* can prevent and/or treat *Streptococcus pneumoniae* infection and have thus completed the present invention.

The gist of the present invention is as follows.
(1) A prophylactic and/or therapeutic agent for *Streptococcus pneumoniae* infection, comprising a bacterium belonging to the genus *Enterococcus*.
(2) The prophylactic and/or therapeutic agent for *Streptococcus pneumoniae* infection of (1), wherein the bacterium belonging to the genus *Enterococcus* is a *Lactococcus*.
(3) The prophylactic and/or therapeutic agent for *Streptococcus pneumoniae* infection of (2), wherein the *Lactococcus* is *Enterococcus fecalis*.
(4) The prophylactic and/or therapeutic agent for *Streptococcus pneumoniae* infection of (3), wherein the *Enterococcus fecalis* is EF-2001 strain.
(5) The prophylactic and/or therapeutic agent for *Streptococcus pneumoniae* infection of any one of (1)-(4), wherein the bacterium belonging to the genus *Enterococcus* is killed.
(6) The prophylactic and/or therapeutic agent for *Streptococcus pneumoniae* infection of any one of (1)-(5), wherein the bacterium belonging to the genus *Enterococcus* is orally administered.
(7) The prophylactic and/or therapeutic agent for *Streptococcus pneumoniae* infection of (6), wherein the bacterium belonging to the genus *Enterococcus* is orally administered in an amount of $1 \times 10^8$-$1 \times 10^{11}$ CFU/kg body weight per dose.
(8) The prophylactic and/or therapeutic agent for *Streptococcus pneumoniae* infection of (7), wherein the bacterium belonging to the genus *Enterococcus* is orally administered one or more times per day in an amount of $1 \times 10^8$-$1 \times 10^{11}$ CFU/kg body weight per dose.
(9) The prophylactic and/or therapeutic agent for *Streptococcus pneumoniae* infection of (8), wherein the bacterium belonging to the genus *Enterococcus* is orally administered one to five times per day in an amount of $1 \times 10^8$-$1 \times 10^{11}$ CFU/kg body weight per dose.
(10) The prophylactic and/or therapeutic agent for *Streptococcus pneumoniae* infection of (6), wherein the bacterium belonging to the genus *Enterococcus* is orally administered in an amount of $1 \times 10^9$-$5 \times 10^{10}$ CFU/kg body weight per dose.
(11) The prophylactic and/or therapeutic agent for *Streptococcus pneumoniae* infection of (10), wherein the bacterium belonging to the genus *Enterococcus* is orally administered one or more times per day in an amount of $1 \times 10^9$-$5 \times 10^{10}$ CFU/kg body weight per dose.
(12) The prophylactic and/or therapeutic agent for *Streptococcus pneumoniae* infection of (11), wherein the bacterium belonging to the genus *Enterococcus* is orally administered one to five times per day in an amount of $1 \times 10^9$-$5 \times 10^{10}$ CFU/kg body weight per dose.
(13) The prophylactic and/or therapeutic agent for *Streptococcus pneumoniae* infection of (6), wherein the bacterium belonging to the genus *Enterococcus* is orally administered in an amount of $1.2 \times 10^{10}$ or more CFU/kg body weight per dose.
(14) The prophylactic and/or therapeutic agent for *Streptococcus pneumoniae* infection of (13), wherein the bacterium belonging to the genus *Enterococcus* is orally administered one or more times per day in an amount of $1.2 \times 10^{10}$ or more CFU/kg body weight per dose.
(15) The prophylactic and/or therapeutic agent for *Streptococcus pneumoniae* infection of (14), wherein the bacterium belonging to the genus *Enterococcus* is orally administered one to five times per day in an amount of $1.2 \times 10^{10}$ or more CFU/kg body weight per dose.
(16) The prophylactic and/or therapeutic agent for *Streptococcus pneumoniae* infection of any one of (6)-(15), wherein the bacterium belonging to the genus *Enterococcus* is orally administered seven or more days.

(17) The prophylactic and/or therapeutic agent for *Streptococcus pneumoniae* infection of any one of (1)-(16), which is used for prevention of *Streptococcus pneumoniae* infection.
(18) The prophylactic and/or therapeutic agent for *Streptococcus pneumoniae* infection of any one of (1)-(16), which is used for treatment of *Streptococcus pneumoniae* infection.
(19) A medicine for prevention and/or treatment of *Streptococcus pneumoniae* infection, comprising a bacterium belonging to the genus *Enterococcus*.
(20) A food for prevention and/or treatment of *Streptococcus pneumoniae* infection, comprising a bacterium belonging to the genus *Enterococcus*.
(21) A method for prevention and/or treatment of *Streptococcus pneumoniae* infection, comprising administering to a subject a pharmaceutically effective amount of a bacterium belonging to the genus *Enterococcus*.
(22) Use of a bacterium belonging to the genus *Enterococcus* for prevention and/or treatment of *Streptococcus pneumoniae* infection.
(23) A bacterium belonging to the genus *Enterococcus* for use in a method for prevention and/or treatment of *Streptococcus pneumoniae* infection.

Advantageous Effects of Invention

The present invention enables prevention and/or treatment of *Streptococcus pneumoniae* infection.

The present specification incorporates the contents of the specification and/or drawings of Japanese Patent Application No. 2018-015333 which is a Japanese patent application from which the present application claims priority.

DESCRIPTION OF EMBODIMENTS

Figure 1:
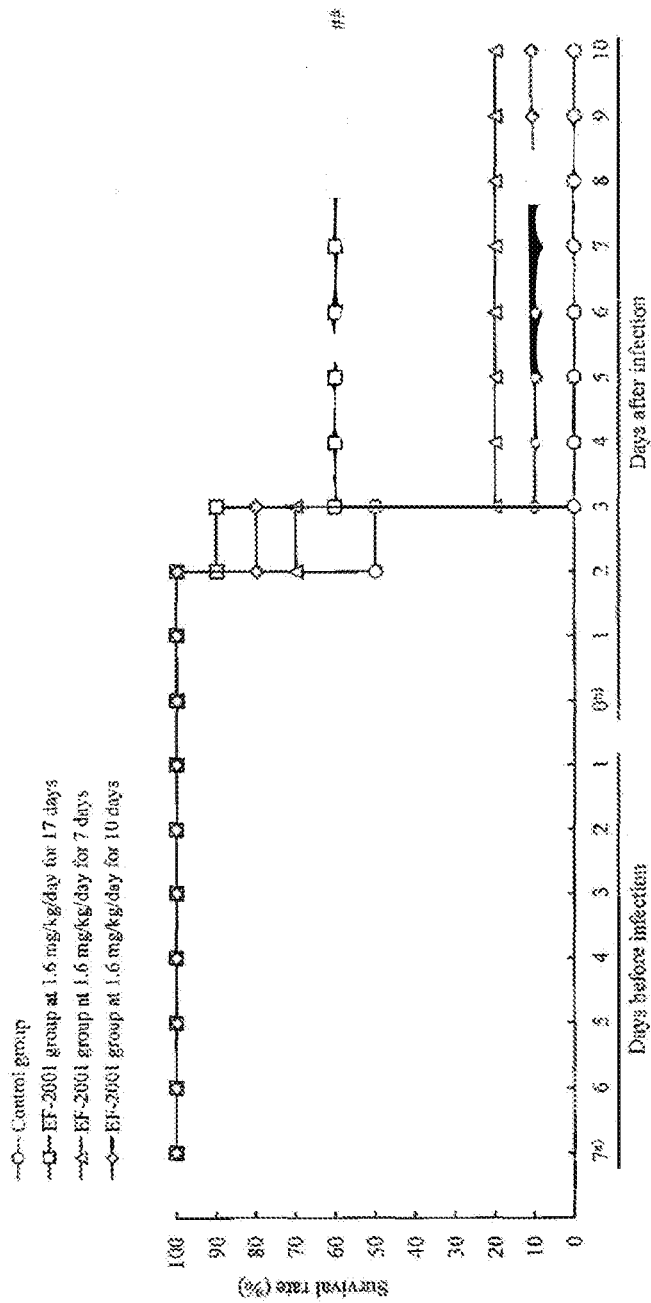
FIG. 1 shows a test result (survival rate (results of Kaplan-Meier plot)) in Example 1.

Hereinafter, embodiments of the present invention will be described in more detail.

The present invention provides a prophylactic and/or therapeutic agent for *Streptococcus pneumoniae* infection, comprising a bacterium belonging to the genus *Enterococcus*.

It is recommended that the bacterium belonging to the genus *Enterococcus* be a *lactococcus* (e.g., *Enterococcus faecalis*, *Enterococcus faecium*, *Enterococcus avium*, *Enterococcus gallinarum*, or *Enterococcus casseliflavus*), and preferred is a *lactococcus* having biological response modifier (BRM) activity (YAKUGAKU ZASSHI, 112: 919-925, 1992; YAKUGAKU ZASSHI, 113: 396-399, 1992; Journal of Animal Clinical Research Foundation, 3: 11-20, 1994). *Enterococcus faecalis* is known as a *lactococcus* having BRM activity. *Enterococcus faecalis* EF-2001 strain is available from Nihon Berumu Co., Ltd. (2-14-3 Nagatacho, Chiyoda-ku, Tokyo).

*Enterococcus Faecalis*-2001 strain can be obtained from fecal matter of a normal person and has the following properties.

A Gram-positive coccus. Shape of colony (Trypto-Soya agar medium, 24-hour culture): 1.0-mm diameter, smooth, precise circle, white colony. Bacterial morphology: circular to oval (1.0×1.5 µm). Likely to form chains in liquid media. Non-spore-forming. Facultative anaerobic. Ferments glucose to produce lactic acid (final pH: 4.3). Non-gas-producing. Catalase-negative. Proliferates at 10 to 45° C. (the optimal temperature is 37° C.). Proliferates to pH 9.6, 6.5% NaCl, and 40% bile. Positive for 0.04% potassium tellurite. Positive for 0.01% tetrazolium. Positive for 0.1% methylene blue milk. Hydrolyzes arginine. Ferments amygdalin, cellobiose, fructose, galactose, glucose, glycerol, lactose, maltose, mannose, mannitol, ribose, salicin, sucrose, melicitose, and sorbitol to produce acids. Resistant at 60° C. for 30 minutes. Digests casein and gelatin. Decarboxylates tyrosine into tyramine. Lancefield antigen group: D. GC %: 35.0±1.0%.

The bacterium belonging to the genus *Enterococcus* may be a viable bacterium or a killed bacterium, and the bacterium may be subjected to a destruction treatment (e.g., homogenization, enzyme treatment, or ultrasonication) or any other treatment such as heating or drying (e.g., freeze-drying or spray-drying). The viable bacterium may be killed by heating. The viable bacterium is expected to exhibit effects produced by lactic acid fermentation. The killed bacterium is expected to exhibit an intestinal immunity-activating effect. The particle size of the bacterial cell is typically 0.05 µm-50 µm, preferably 0.08-20 µm, more preferably 0.1-10 µm. The bacterium may be mixed with a diluent, and then a thickener may be added to form granules. It is recommended to select the diluent and thickener from materials approved for addition to foods and medicines.

The prophylactic and/or therapeutic agent for *Streptococcus pneumoniae* infection of the present invention can be used for prevention and/or treatment of *Streptococcus pneumoniae* infection. The prophylactic and/or therapeutic agent for *Streptococcus pneumoniae* infection of the present invention can be used as a medicine or a food additive.

The present invention provides a medicine for prevention and/or treatment of *Streptococcus pneumoniae* infection, comprising a bacterium belonging to the genus *Enterococcus*.

When the agent is used as a medicine, it is recommended that the bacterium belonging to the genus *Enterococcus* be used alone or be mixed with an excipient or a carrier to make a formulation such as a tablet, a capsule, a powder, a granule, a liquid, a syrup, an aerosol, a suppository, or an injection. The excipient or carrier may be any excipient or carrier that is commonly used in the art and is pharmaceutically acceptable, and the type and composition of the excipient or carrier are chosen as appropriate. For example, water or a vegetable oil is used as a liquid carrier. As a solid carrier there is used, for example, a sugar such as lactose, sucrose, or glucose, a starch such as potato starch or corn starch, or a cellulose derivative such as crystalline cellulose. A lubricant such as magnesium stearate, a binder such as gelatin or hydroxypropyl cellulose, and a disintegrant such as carboxymethyl cellulose may also be added. Further, an antioxidant, a colorant, a flavoring agent, a preservative, or the like may also be added. The medicine can also be used as a freeze-dried formulation.

The bacterium belonging to the genus *Enterococcus* can be administered by various routes, such as orally, nasally, rectally, transdermally, subcutaneously, intravenously, and intramuscularly.

The content of the bacterium belonging to the genus *Enterococcus* in the formulation varies depending on the type of the formulation, and is typically 0.001 to 100% by mass and preferably 0.01 to 100% by mass.

The dose of the bacterium belonging to the genus *Enterococcus* may be any pharmaceutically effective amount, i.e., any amount sufficient to exert the MRSA infection protective effect, and varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, in terms of the amount of the bacterium belonging to the genus *Enterococcus*, and to give one to several (e.g., 2, 3, 4, or 5 times) administrations per day.

The bacterium belonging to the genus *Enterococcus* may be added to a food. The present invention provides a food for prevention and/or treatment of *Streptococcus pneumoniae* infection, comprising a bacterium belonging to the genus *Enterococcus*.

The following may be added to the food of the present invention: general ingredients such as protein, fat, carbohydrate, and sodium; minerals such as potassium, calcium, magnesium, and phosphorus; trace elements such as iron, zinc, copper, selenium, and chromium; vitamins such as vitamin A, β-carotene, vitamin $B_1$, vitamin $B_2$, vitamin $B_6$, vitamin $B_{12}$, vitamin C, niacin, folic acid, vitamin $D_3$, vitamin E, biotin, and pantothenic acid; and other substances such as coenzyme Q10, α-lipoic acid, galacto-oligosaccharide, dietary fiber, an excipient (such as water, carboxymethyl cellulose, or lactose), a sweetener, a flavoring agent (such as malic acid, citric acid, or amino acid), and a fragrance. When the food of the present invention is provided as a liquid food, water, saline solution, fruit juice, or the like can be used as a liquid in which the food ingredients are dispersed or dissolved. In order to improve the taste in oral administration, it is recommended to use fruit juice.

The food of the present invention may be in any form such as a powder, a granule, a tablet, or a liquid. In order to allow sick or old persons to easily take the food, it is preferable for the food to be a gelled product such as jelly.

Gelling agents that can be used include thickening polysaccharides such as dextrin, agar, xanthan gum, locust bean gum, carrageenan, and pectin, gellan gum, psyllium seed gum, tara gum, guar gum, glucomannan, alginic acid, tamarind seed gum, and cellulose, and it is preferable to use one or two or more thickening polysaccharides. As regards the gel strength of the gelled product, it is preferable that the gel strength at 5° C. be 7,000±2,000 N/m². When the gel strength is 7,000±2,000 N/m², it is more preferable that the adhesion energy be 60±40 J/m³ and the cohesiveness be 0.7±0.1 J/m³. Such a gel with low adhesiveness and high cohesiveness has excellent swallowability.

The gel strength can be measured as follows. A texturometer of YAMADEN Co., Ltd. and a 16-mm-diameter plunger are used as gel strength measurement instruments, and the measurement is carried out under the following conditions: the measurement temperature is 25° C., the compression speed (the speed at which the plunger is pushed in) is 10 mm/s, the measurement strain (the ratio of the amount of pushing-in to the sample thickness) is 40.00%, the distance over which the plunger is pushed in is 10.00 mm, and the number of repetitions of pushing-in of the plunger is two.

The adhesion energy is measured as a negative energy required for pulling out the plunger after the first pushing-in of the plunger in the above gel strength measurement.

The cohesiveness is measured as the ratio between the energy at the first pushing-in and the energy at the second pushing-in in the above gel strength measurement.

The intake of the bacterium belonging to the genus *Enterococcus* may be any amount sufficient to exert an effect for prevention and/or treatment of *Streptococcus pneumoniae* infection, and varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, in terms of the amount of the bacterium belonging to the genus *Enterococcus*, and to give one to several (e.g., 2, 3, 4, or 5 times) administrations per day.

EXAMPLES

Hereinafter, the present invention will be described in detail based on Examples. The present invention is not limited to these Examples.

Figure 6:
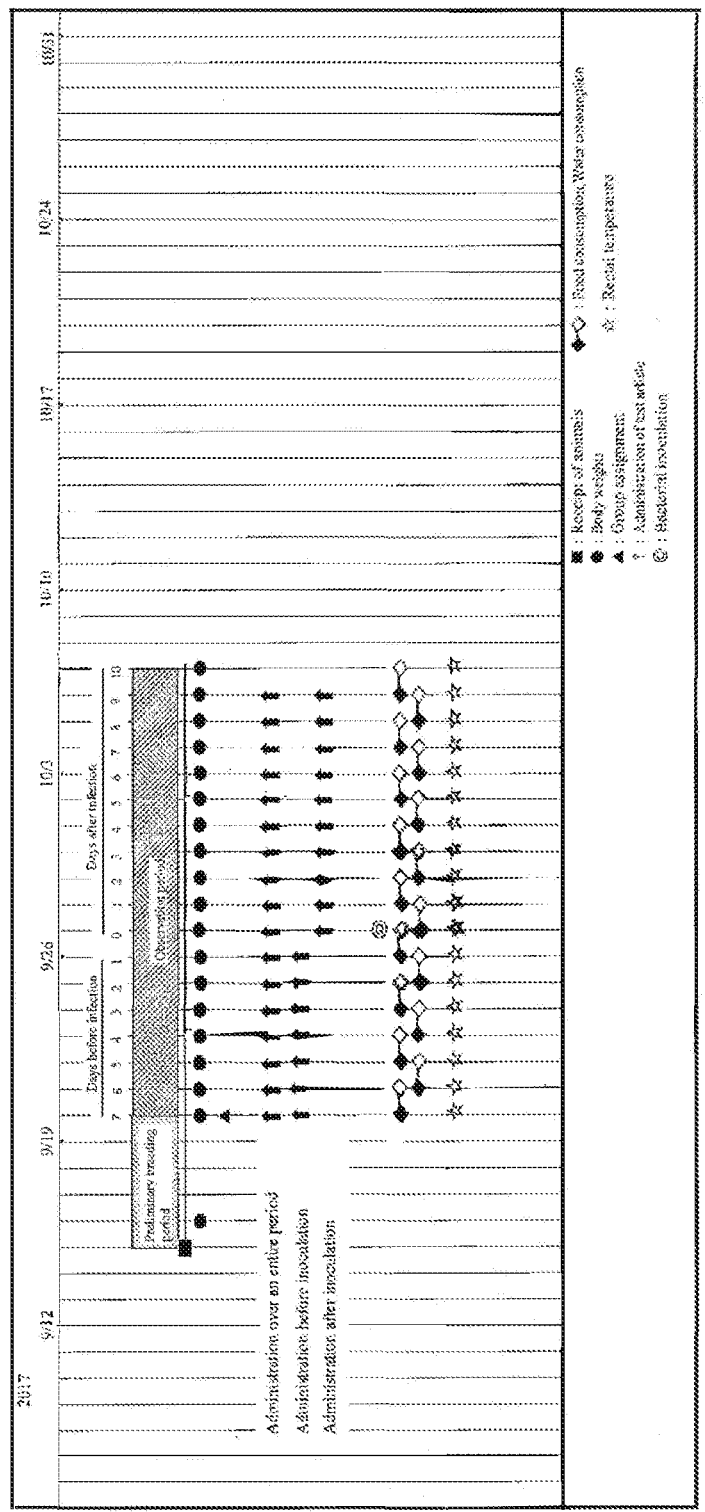
FIG. 6 shows the test schedule in Example 1.

[Example 1] Administration Effects of Heat-Killed Lactic Acid Bacteria *E. faecalis* on *Streptococcus pneumoniae*-Infected Mice Mice were infected with *Streptococcus pneumoniae* and administered with heat-killed lactic acid bacteria *E. faecalis* orally to study its preventive and therapeutic effects.
(Test Schedule)
The test schedule is shown in FIG. 6
(Materials and Methods)
Test Substance and Medium
Test Substance
Name: LACTIC ACID BACTERIA POWDER EF-2001 (Nihon Berumu Co., Ltd.) (heat-killed *E. faecalis*, 500 nm=0.5 μm in diameter)
Properties: Yellow-brown powder
Storage conditions: Room temperature, light-shielded, moisture-proof
Controlled temperature: 18.0-28.0° C.
Medium
Name: Water for injection
Storage Conditions: Room Temperature
Controlled temperature: 18.0-28.0° C.
Manufacturer: Otsuka Pharmaceutical Factory, Inc.
Sample
Method of Preparation of Test Substance
Lactic acid bacteria powder EF-2001 was weighed in 20 mg (electronic balance: XP205DR, Mettler-Toledo Co., Ltd.) and suspended in water for injection. The suspension was diluted to give a total volume of 125 mL with a concentration of 0.16 mg/mL. Since the lactic acid bacteria powder precipitated, it was stirred well enough to be kept suspended. Preparation was made just before use.
Pathogenic Microorganism
Strain Used
*Streptococcus pneumoniae* (ATCC 6303)
Storage Conditions
Cryopreserved in an Ultra-cold freezer (controlled temperature: −90 to −70° C., MDF-394AT, Sanyo Electric Co., Ltd.) until use.
Reagents
(1) Sheep blood agar (Nippon BectonDickinson Company, Ltd.)
(2) Physiological saline (Otsuka Pharmaceutical Plant, Inc.)

Preculture

The preserved strain was thawed and plated on a sheep blood agar, then placed in an anaerobic jar containing a carbon dioxide generator for culture with carbon dioxide (Anelopack $CO_2$, Mitsubishi Gas Chemical Co., Ltd.) and cultured in an incubator (ILE800, Yamato Science Co., Ltd.) at 37° C. for 2 days. Then, physiological saline was added to release the bacterial cells. The released bacterial cells were filtered through a sterile mesh (100 μm, Cell Strainer: FALCON (registered trademark)) to remove bacterial cell masses and impurities. The filtrate was used as a stock solution of liquid bacterial inoculum. This stock solution was stored in a refrigerator (controlled temperature: 2.0° C. to 8.0° C., UKS-3610DHC, Nippon Freezer Co., Ltd.) until the day of inoculation with the liquid bacterial inoculum.

Viable Cell Count in the Stock Solution

The stock solution was diluted $10^2$-, $10^4$- or $10^6$-folds with physiological saline. The $10^4$- and $10^6$-fold diluted solutions were smeared on the sheep blood agar, placed in the anaerobic jar containing a carbon dioxide generating agent for culture with $CO_2$ gas, and cultured in the incubator at 37° C. for a day. The number of colonies after culture was counted with a handy colony counter (CC-1, Azwan Co., Ltd.), and the number of viable bacterial cells contained in 1 ml of the stock solution was calculated.

Preparation of a Liquid Bacterial Inoculum

The stock solution was diluted with physiological saline to a concentration of $1 \times 10^2$ CFU/mL at the day of inoculation. The thus prepared bacterial solution was used as a liquid bacterial inoculum. The number of viable bacterial cells in the liquid bacterial inoculum was counted according to the method shown in the "Viable bacterial cell count in the stock solution."

Animal Test System

Animal Species, Lineage

Species: Mice (SPF)

Lineage: BALB/c strain (BALB/c Cr Slc)

Sex, Age, and Number of Animals Acquired

Female, 4 weeks old, 44 mice

Body Weight Range 1 Day after Acquisition of Animals 13.4-17.9 g

Source

Japan SLC, Inc.

Preliminary Feeding

The animals were preliminarily fed for five days. During this period, their general condition was observed once a day and the body weight was measured twice (both at the day next to the acquisition of animals and at the day when the preliminary feeding period ended) by electronic balance (PB3002-S/FACT, Metler Toledo Inc.). Animals with no abnormalities in body weight change and general condition were used for grouping.

Grouping Methods

The animals were stratified by body weight using a computer program and then at the day of grouping, random sampling was applied to ensure that the mean body weight and variance of the respective groups were approximately equal.

Identification Methods

Animals were identified by two methods in combination that were applied at the day of their acquisition: filling out on the tails with oil-based ink and painting colors on the limbs with oil-based ink. After grouping, the animals were identified by filling out animal numbers on the tails with oil-based ink. Each cage was fitted with two kinds of label, one being applied during the preliminary feeding period and filled with test number, date of animal acquisition, and animal number for preliminary feeding, and the other being color-coded labels applied after grouping and filled with test number, group name, and animal number.

Environmental Conditions and Rearing Management

Animals were reared in a room (Kiso Sansen Branch, Room No. 1) maintained at a temperature of 18-28° C. (measured value: 20-27° C.), a humidity of 30-80% (measured value: 45-73%), and light/dark periods, each 12 hours (lighting applied: 6:00 a.m. to 6:00 p.m.). Animals were reared individually in stainless steel cages (W:100×D:160× H:80 mm) both during the preliminary feeding period and after grouping.

Cages and feeders were changed at least once a week, and water bottles and dishes were changed at least twice a week. The room was cleaned up daily by wiping and disinfecting the floor with a disinfectant-soaked mop.

Feed

The animals were fed ad libitum with a solid diet (CRF-1, Oriental Yeast Co., Ltd.) placed in feeders; the diet was manufactured within 5 months before the experiment.

Contaminant levels, bacterial counts, and nutrient contents of the diet were confirmed to meet the acceptance criteria of the test facility for each lot of diet.

Drinking Water

The animals were allowed to drink tap water ad libitum as it was supplied from a water bottle. Contaminant levels and bacterial counts of drinking water were analyzed almost every 6 months to ensure that they met the acceptance criteria of the test facility.

Administration

Route of Administration: Oral

Administration Method

A 1 mL disposable syringe (Terumo Co., Ltd.) equipped with a mouse feeding needle (FUCHIGAMI) was used to perform forced oral administration. At the time of administration, the required amount was collected by stirring the sample.

Dosage Volume, Time of Day, Number of Doses, and Period of Administration

Dosage volume was calculated in 10 mL/kg based on the body weight of animal at the day of administration.

The administration was started at 11:00 a.m. and continued sequentially beginning in Group 1.

The number of doses was set as once a day. (17 doses in total for Groups 1 and 2, 7 doses for Group 3, and 10 doses for Group 4, respectively).

The date at which the administration started was calculated as day 1. Groups 1 and 2 were dosed for 7 days before inoculation and 10 days after inoculation whereas Group 3 was dosed for 7 days before inoculation. Group 4 was dosed for 10 days after inoculation.

Grouping

The number of animals and group composition are shown in the table below.

| Group | Group name | Color of label | Dose (mg/ kg/day) | Administration Period | Number of animals (animal number) |
|---|---|---|---|---|---|
| 1 | CONTROL (0 mg/125 mL) | White | 0* | 17 days including pre- and post-inoculation periods | 10 (F01151 - F01160) |

-continued

| Group | Group name | Color of label | Dose (mg/ kg/day) | Administration Period | Number of animals (animal number) |
|---|---|---|---|---|---|
| 2 | LACTIC ACID BACTERIA POWDER EF-2001 (80 mg/125 mL) (all-period administration) | Red | 1.6 | 17 days including pre- and post-inoculation periods | 10 (F02251 - F02260) |
| 3 | LACTIC ACID BACTERIA POWDER EF-2001 (80 mg/125 mL) (administered before inoculation) | Blue | 1.6 | 7 days before inoculation | 10 (F03351- F03360) |
| 4 | LACTIC ACID BACTERIA POWDER EF-2001 (80 mg/125 mL) (administered after inoculation) | Yellow | 1.6 | 10 days from the day of inoculation | 10 (F04451 - F04460) |

*The medium, water for injection, was administered.

Administration to mice with lactic acid bacteria powder EF-2001 at a dose of 80 mg/125 mL once a day is equivalent to a dose of $1.2 \times 10^{10}$ CFU/kg/day.

Method of Inoculation of Bacterial Solution

Seven days after grouping, 0.5 mL (50 CFU) of the bacterial solution was inoculated intraperitoneally using a 1-mL volume disposable syringe (Terumo Co., Ltd.) attached to a 27 G injection needle (Terumo Co., Ltd.). The bacterial solution was stirred for use in each inoculation. Inoculation was performed 2 hours before administration of the test substance.

Observation and Examination

Observation of General Condition

The general condition of the mice was observed once a day before the administration of the test substance for the period from the day of grouping to the day before the inoculation, 4 times a day (i.e., twice in the morning and twice in the afternoon before administration of the test substance) for the period from the day of the inoculation to 3 days after the inoculation, and twice a day (i.e., once in the morning before administration of the test substance and once in the afternoon) at day 4 post-inoculation and thereafter.

The first observation in the morning of the day of inoculation was performed before the inoculation.

Measurement of Rectal Temperature

After the day of grouping but before administration of the test substance (after the first observation of general condition in the morning), rectal temperature was measured with a thermometer (Physitemp, Model BAT-12, PHYSITEMP INSTRUMENTS INC.). To measure, the sensor with a coating of petrolatum was inserted into the anus of the mouse, and the rectal temperature was measured.

Measurement of Body Weight

Following the day of grouping, body weight was measured every day with an electronic balance (PB3002-S/ FACT, Mettler-Toledo Co., Ltd.) before administration of the test substance (after the first observation of general condition in the morning.)

Measurement of Feed Intake and Water Intake

Following the day of grouping, the amounts of feed and water inclusive of the feeder and water supply bottle were measured every day with an electronic balance (PB3002-S/ FACT, Mettler-Toledo Co., Ltd.) and the amounts remaining in the feeder and water supply bottle were measured on the following day. Feed intake (or water intake) per day was calculated from the difference between the amount of feed (or water) and the amount remaining in the feeder (or water supply bottle).

Statistical Method

The survival rate was calculated for each group. For the rectal temperature, body weight, feed intake and water intake, the average and standard deviation in each group were calculated. A Fisher's exact test was conducted as a significance test for the survival rate on each day of observation as between the control group and each of the other groups. A Kaplan-Meier plot was drawn over the entire observation period, and a Logrank test was conducted, with Holm corrections being made for comparisons between groups to adjust for multiplicity.

Multiple comparisons were performed for the rectal temperature, body weight, feed intake, and water intake. That is, a test of equal variance by Bartlett method was carried out, and Tukey's test was carried out in the case of equal variance. On the other hand, when no equal variance was observed, Steel-Dwass test was used.

A hazard rate of 5% was considered significant, and separate indications were given for a hazard rate less than 5% and a hazard rate less than 1%. A commercially-sold statistical program (SAS system, SAS Institute Japan) was used for the statistical analysis.

(Test Results)

General Condition

The results are shown in Table 1. For survival rate, the results of Kaplan-Meier plot are shown in FIG. 1.

TABLE 1

Clinical signs

| Group | mg/kg/day | Period for administration | Number of animals and clinical signs | Days before infection | | | | | | |
|---|---|---|---|---|---|---|---|---|---|---|
| | | | | 7[a] | 6 | 5 | 4 | 3 | 2 | 1 |
| Control | 0 | 17 | Number of animals | 10 | 10 | 10 | 10 | 10 | 10 | 10 |
| | | | Normal | 10 | 10 | 10 | 10 | 10 | 10 | 10 |
| | | | Coarse fur | 0 | 0 | 0 | 0 | 0 | 0 | 0 |
| | | | Decrease in locomotor activity | 0 | 0 | 0 | 0 | 0 | 0 | 0 |
| | | | Death | 0 | 0 | 0 | 0 | 0 | 0 | 0 |
| EF-2001 | 1.6 | 17 | Number of animals | 10 | 10 | 10 | 10 | 10 | 10 | 10 |
| | | | Normal | 10 | 10 | 10 | 10 | 10 | 10 | 10 |
| | | | Coarse fur | 0 | 0 | 0 | 0 | 0 | 0 | 0 |
| | | | Decrease in locomotor activity | 0 | 0 | 0 | 0 | 0 | 0 | 0 |
| | | | Death | 0 | 0 | 0 | 0 | 0 | 0 | 0 |
| | 1.6 | 7 | Number of animals | 10 | 10 | 10 | 10 | 10 | 10 | 10 |
| | | | Normal | 10 | 10 | 10 | 10 | 10 | 10 | 10 |
| | | | Coarse fur | 0 | 0 | 0 | 0 | 0 | 0 | 0 |
| | | | Decrease in locomotor activity | 0 | 0 | 0 | 0 | 0 | 0 | 0 |
| | | | Death | 0 | 0 | 0 | 0 | 0 | 0 | 0 |
| | 1.6 | 10 | Number of animals | 10 | 10 | 10 | 10 | 10 | 10 | 10 |
| | | | Normal | 10 | 10 | 10 | 10 | 10 | 10 | 10 |
| | | | Coarse fur | 0 | 0 | 0 | 0 | 0 | 0 | 0 |
| | | | Decrease in locomotor activity | 0 | 0 | 0 | 0 | 0 | 0 | 0 |
| | | | Death | 0 | 0 | 0 | 0 | 0 | 0 | 0 |

[a] Start of administration in the control group, the EF-2001 group at 1.6 mg/kg/day for 17 days and the EF-2001 group at 1.6 mg/kg/day for 7 days.

| Group | mg/kg/day | Period for administration | Number of animals and clinical signs | Days after infection | | | | | | | | | | | | | | | |
|---|---|---|---|---|---|---|---|---|---|---|---|---|---|---|---|---|---|---|---|
| | | | | 0[a] | | | | 1 | | | | 2 | | | | 3 | | | |
| | | | | AM1 | AM2 | PM1 | PM2 | AM1 | AM2 | PM1 | PM2 | AM1 | AM2 | PM1 | PM2 | AM1 | AM2 | PM1 | PM2 |
| Control | 0 | 17 | Number of animals | 10 | 10 | 10 | 10 | 10 | 10 | 10 | 10 | 5 | 6 | 6 | 6 | 4 | 4 | 4 | 0 |
| | | | Normal | 10 | 10 | 10 | 10 | 3 | 3 | 3 | 3 | 0 | 0 | 0 | 0 | 0 | 0 | 0 | — |
| | | | Coarse fur | 0 | 0 | 0 | 0 | 7 | 7 | 7 | 7 | 4 | 6 | 6 | 5 | 4 | 4 | 0 | — |
| | | | Decrease in locomotor activity | 0 | 0 | 0 | 0 | 0 | 0 | 0 | 0 | 4 | 2 | 2 | 1 | 0 | 0 | 0 | — |
| | | | Death | 0 | 0 | 0 | 0 | 0 | 0 | 0 | 0 | 1 | 2 | 2 | 4 | 0 | 0 | 3 | — |
| EF-2001 | 1.6 | 17 | Number of animals | 10 | 10 | 10 | 10 | 10 | 10 | 10 | 10 | 9 | 9 | 9 | 9 | 7 | 7 | 7 | 7 |
| | | | Normal | 10 | 10 | 10 | 10 | 6 | 6 | 5 | 5 | 3 | 4 | 4 | 4 | 3 | 3 | 3 | 3 |
| | | | Coarse fur | 0 | 0 | 0 | 0 | 4 | 4 | 5 | 5 | 4 | 5 | 5 | 5 | 4 | 4 | 4 | 4 |
| | | | Decrease in locomotor activity | 0 | 0 | 0 | 0 | 0 | 0 | 0 | 0 | 2 | 1 | 1 | 1 | 1 | 1 | 1 | 0 |
| | | | Death | 0 | 0 | 0 | 0 | 0 | 0 | 0 | 0 | 1 | 0 | 0 | 0 | 0 | 0 | 0 | 1 |
| | 1.6 | 7 | Number of animals | 10 | 10 | 10 | 10 | 10 | 10 | 10 | 10 | 7 | 7 | 7 | 7 | 4 | 4 | 4 | 3 |
| | | | Normal | 10 | 10 | 10 | 10 | 4 | 4 | 5 | 5 | 2 | 3 | 2 | 2 | 2 | 2 | 2 | 2 |
| | | | Coarse fur | 0 | 0 | 0 | 0 | 5 | 5 | 4 | 5 | 5 | 4 | 5 | 5 | 2 | 2 | 1 | 0 |
| | | | Decrease in locomotor activity | 0 | 0 | 0 | 0 | 1 | 1 | 1 | 0 | 3 | 1 | 1 | 2 | 1 | 2 | 2 | 3 |
| | | | Death | 0 | 0 | 0 | 0 | 0 | 0 | 0 | 0 | 0 | 0 | 0 | 0 | 1 | 0 | 1 | 1 |

[a] Start of administration in the control group, the EF-2001 group at 1.6 mg/kg/day for 17 days and the EF-2001 group at 1.6 mg/kg/day for 7 days.

TABLE 1-continued

Clinical signs

| Group | mg/kg/day | Period for administration | Number of animals and clinical signs | 4 AM | 4 PM | 5 AM | 5 PM | 6 AM | 6 PM | 7 AM | 7 PM | 8 AM | 8 PM | 9 AM | 9 PM | 10 AM | 10 PM |
|---|---|---|---|---|---|---|---|---|---|---|---|---|---|---|---|---|---|
| | 1.6 | 10 | Number of animals | 10 | 10 | 10 | 10 | 10 | 10 | 10 | 10 | 8 | 8 | 8 | 4 | 4 | 3 |
| | | | Normal | 10 | 10 | 10 | 10 | 9 | 9 | 7 | 2 | 1 | 0 | 0 | 0 | 0 | 0 |
| | | | Coarse fur | 0 | 0 | 0 | 0 | 1 | 1 | 3 | 6 | 7 | 8 | 4 | 4 | 3 | 1 |
| | | | Decrease in locomotor activity | 0 | 0 | 0 | 0 | 0 | 0 | 0 | 2 | 2 | 2 | 2 | 3 | 2 | 0 |
| | | | Death | 0 | 0 | 0 | 0 | 0 | 0 | 0 | 2 | 0 | 0 | 4 | 0 | 1 | 2 |

AM1: 1st observation in the morning,
AM2: 2nd observation in the morning,
PM1: 1st observation in the afternoon,
PM2: 2nd observation in the afternoon,
AM: Morning,
PM: Afternoon.
[a] Start of administration in the EF-2001 group at 1.6 mg/kg/day for 10 days.

Days after infection

| Group | mg/kg/day | Period for administration | Number of animals and clinical signs | 4 AM | 4 PM | 5 AM | 5 PM | 6 AM | 6 PM | 7 AM | 7 PM | 8 AM | 8 PM | 9 AM | 9 PM | 10 AM | 10 PM |
|---|---|---|---|---|---|---|---|---|---|---|---|---|---|---|---|---|---|
| Control | 0 | 17 | Number of animals | 0 | 0 | 0 | 0 | 0 | 0 | 0 | 0 | 0 | 0 | 0 | 0 | 0 | 0 |
| | | | Normal | — | — | — | — | — | — | — | — | — | — | — | — | — | — |
| | | | Coarse fur | — | — | — | — | — | — | — | — | — | — | — | — | — | — |
| | | | Decrease in locomotor activity | — | — | — | — | — | — | — | — | — | — | — | — | — | — |
| | | | Death | — | — | — | — | — | — | — | — | — | — | — | — | — | — |
| EF-2001 | 1.6 | 17 | Number of animals | 6 | 6 | 6 | 6 | 6 | 6 | 6 | 6 | 6 | 6 | 6 | 6 | 6 | 6 |
| | | | Normal | 6 | 6 | 6 | 6 | 6 | 6 | 6 | 6 | 6 | 6 | 6 | 6 | 6 | 6 |
| | | | Coarse fur | 0 | 0 | 0 | 0 | 0 | 0 | 0 | 0 | 0 | 0 | 0 | 0 | 0 | 0 |
| | | | Decrease in locomotor activity | 0 | 0 | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 | 0 | 0 |
| | 1.6 | 7 | Number of animals | 2 | 2 | 2 | 2 | 2 | 2 | 2 | 2 | 2 | 2 | 2 | 2 | 2 | 2 |
| | | | Normal | 2 | 2 | 2 | 2 | 2 | 2 | 2 | 2 | 2 | 2 | 2 | 2 | 2 | 2 |
| | | | Coarse fur | 0 | 0 | 0 | 0 | 0 | 0 | 0 | 0 | 0 | 0 | 0 | 0 | 0 | 0 |
| | | | Decrease in locomotor activity | 0 | 0 | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 | 0 | 0 |
| | 1.6 | 10 | Number of animals | 1 | 1 | 1 | 1 | 1 | 1 | 1 | 1 | 1 | 1 | 1 | 1 | 1 | 1 |
| | | | Normal | 1 | 1 | 1 | 1 | 1 | 1 | 1 | 1 | 1 | 1 | 0 | 0 | 0 | 0 |
| | | | Coarse fur | 0 | 0 | 0 | 0 | 0 | 0 | 0 | 0 | 0 | 0 | 1 | 1 | 1 | 1 |
| | | | Decrease in locomotor activity | 0 | 0 | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 | 0 | 0 |

AM: Morning,
PM: Afternoon.

The observation of general condition showed coarse hair and decreased locomotor activity in all groups. Mice died following 2 to 3 days after the inoculation in all groups.

In the control group, coarse hair was observed from 1 day after the inoculation and decreased locomotor activity was observed following 2 days after the inoculation. Five mice died 2 days after the inoculation and 5 mice died 3 days after the inoculation. The survival rate 3 days after the inoculation was 0%.

In the all-period administration group, coarse hair was observed following 1 day after the inoculation, and decreased locomotor activity was observed following 2 days after the inoculation. The number of animals with these symptoms was smaller in the all-period administration group than in the control group. One mouse died 2 days after the inoculation and 3 mice died 3 days after the inoculation. The survival rate at day 3 post-inoculation and thereafter was 60%. At day 3 post-inoculation and thereafter, the survival rate of the all-period administration group increased significantly (Fisher's exact test) compared with the control group, and a significant increase was also observed throughout the observation period (Logrank test).

In the pre-inoculation administration group, coarse hair was observed following 1 day after the inoculation, and decreased locomotor activity was also observed following 2 days after the inoculation. The number of mice with these symptoms was smaller in the pre-inoculation administration group than in the control group. Three mice died 2 days after the inoculation and 5 mice died 2 days after the inoculation. The survival rate at day 3 post-inoculation and thereafter was 20%.

In the post-inoculation administration group, coarse hair was observed following 1 day after the inoculation, and decreased locomotor activity was observed following 2 days after the inoculation. The numbers of mice with these symptoms were comparable to those in the control group. Two mice died 2 days after the inoculation and 7 mice died 3 days after the inoculation. The survival rate at day 3 post-inoculation and thereafter was 10%.

Measurement of Rectal Temperature

Figure 2:
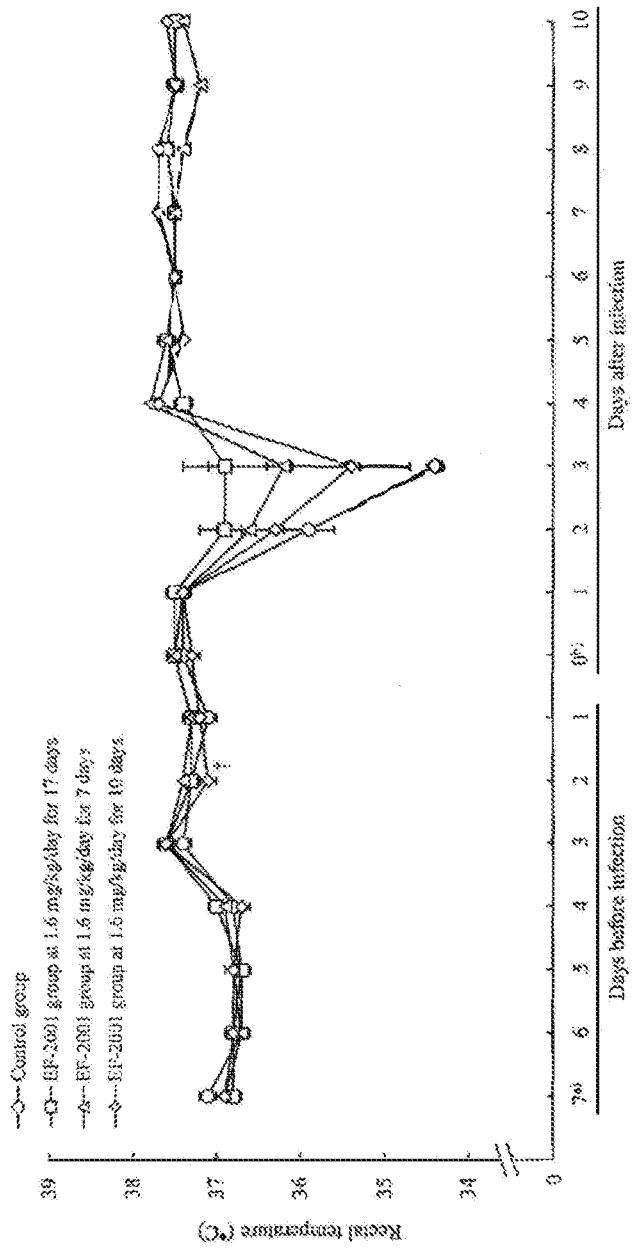
FIG. 2 shows a test result (rectal temperature) in Example 1.

The results are shown in FIG. 2.

In the control group, the mean rectal temperature continued to decrease following 2 to 3 days after the inoculation, leading to a 3° C. decrease in two days.

In the all-period administration group, the mean rectal temperature decreased by 0.6° C. following 2 days after the inoculation. At day 4 post-inoculation and thereafter, the change in rectal temperature was comparable to that before the inoculation.

In the pre-inoculation administration group, the mean rectal temperature decreased 2 and 3 days after the inoculation, leading to a 1.2° C. decrease in two days. At day 4 post-inoculation and thereafter, the change in rectal temperature was comparable to that before the inoculation.

In the post-inoculation administration group, the mean rectal temperature decreased 2 and 3 days after the inoculation, leading to a 2.0° C. decrease in two days. At day 4 post-inoculation and thereafter, the change in rectal temperature was comparable to that before the inoculation.

Body Weight

Figure 3:
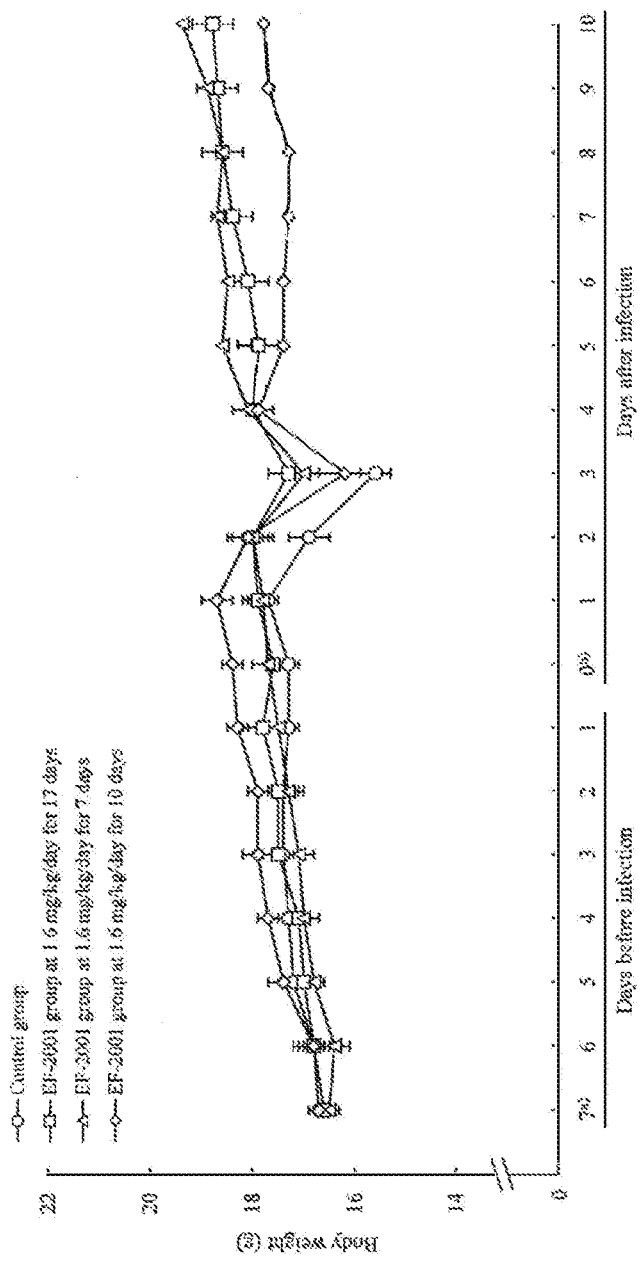
FIG. 3 shows a test result (body weight) in Example.

The results are shown in FIG. 3.

In the control group, the mean body weight decreased by 0.8 g following 2 days after the inoculation and further decreased by 1.3 g following 3 days after the inoculation.

In the all-period administration group, the mean body weight decreased by 0.7 g following 3 days after the inoculation but thereafter changed in a normal way. In the pre-inoculation administration group, the mean body weight decreased by 1.0 g following 3 days after the inoculation but thereafter changed in a normal way.

In the post-inoculation administration group, the mean body weight decreased by 0.6 g following 2 days after the inoculation and stilled decreased by 1.9 g following 3 days after the inoculation but thereafter changed in a normal way.

Feed Intake

Figure 4:
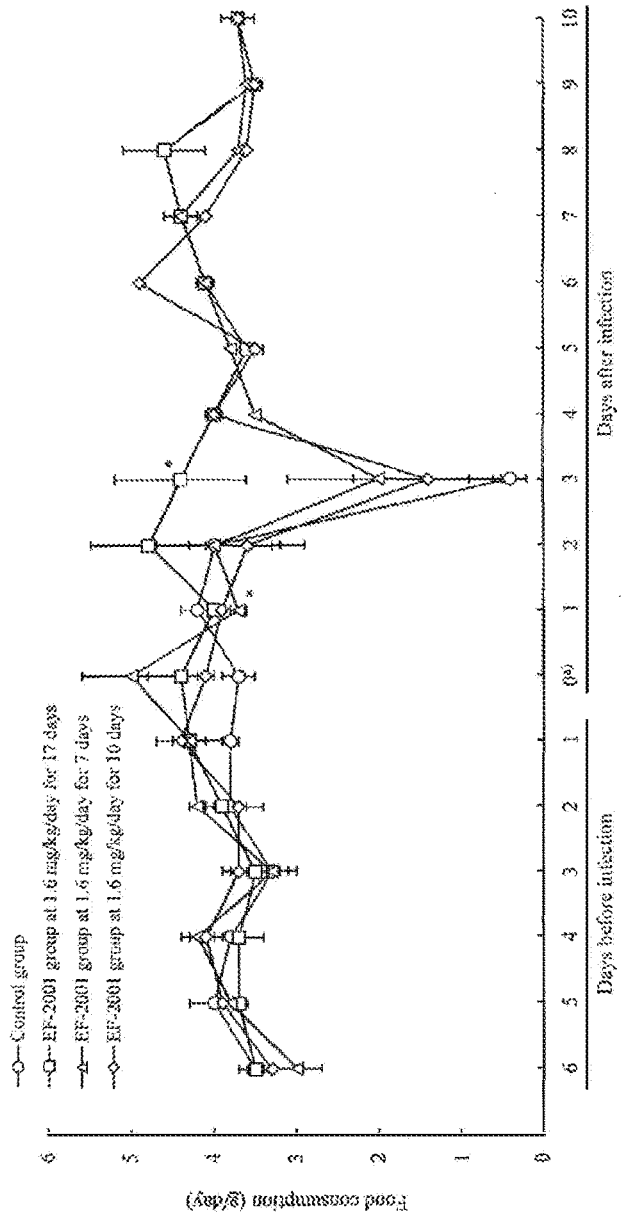
FIG. 4 shows a test result (feed intake) in Example 1.

The results are shown in FIG. 4.

In the control group, the mean feed intake decreased by 3.6 g following 3 days after the inoculation.

In the all-period administration group, there was little change in mean feed intake. Compared with the control group, significant increases were observed following 3 days after the inoculation.

In the pre-inoculation administration group, the mean feed intake decreased by 2.0 g following 3 days after the inoculation but recovered thereafter. Compared with the control group, a significant reduction was observed following 1 day after the inoculation.

In the post-inoculation administration group, the mean feed intake decreased by 2.2 g following 3 days after the inoculation but recovered thereafter.

Water Intake

Figure 5:
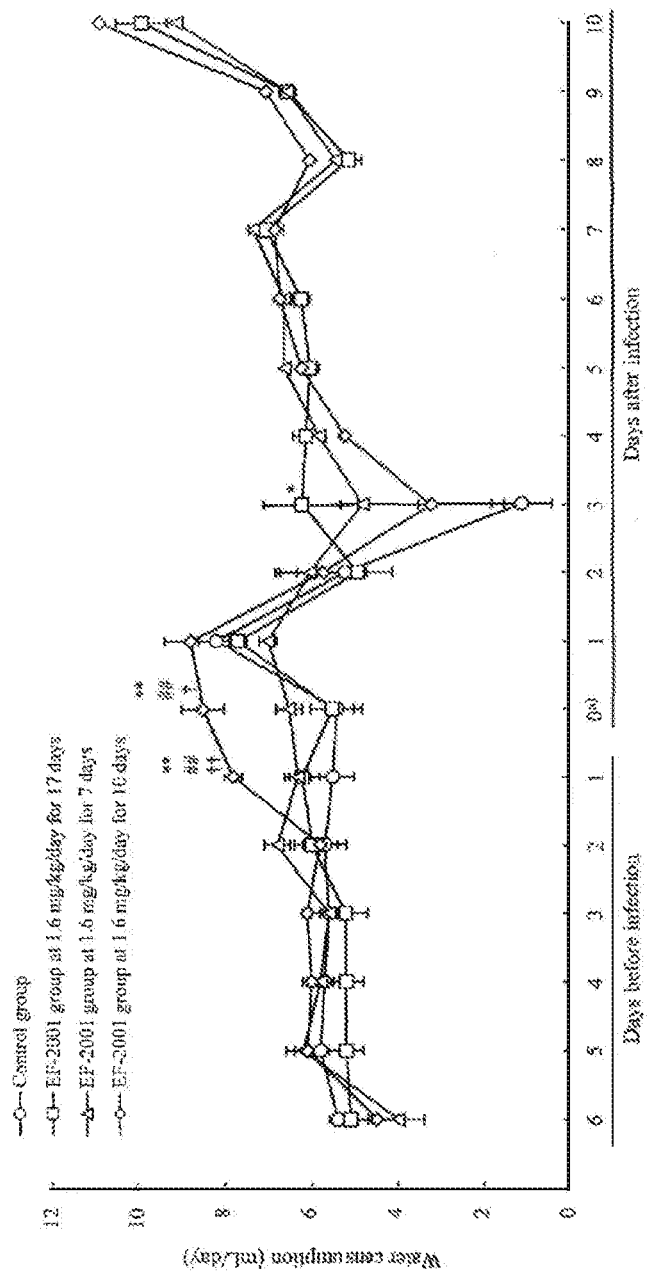
FIG. 5 shows a test result (water intake) in Example 1.

The results are shown in FIG. 5.

In the control group, the mean water intake continued to decrease following 2 to 3 days after the inoculation, leading to a 7.1 ml decrease in two days.

In the all-period administration group, the mean water intake decreased by 2.8 ml following 2 days after the inoculation but recovered thereafter. Compared with the control group, significant increases were observed following 3 days after the inoculation.

In the pre-inoculation administration group, the mean water intake varied by smaller amounts but it continued to decrease following 2 to 3 days after the inoculation, leading to a 2.2 ml decrease in two days; however, a subsequent recovery was observed.

In the post-inoculation administration group, the mean water intake continued to decrease following 2 to 3 days after the inoculation, leading to a 5.6 ml decrease in two days; however, a subsequent recovery was observed. Compared with the control group, all-period administration group, and pre-inoculation administration group, significant increases were observed both 1 day before the inoculation and at the day of the inoculation.

(Discussion)

In the control group, abnormalities in general condition, decreases in body weight, feed intake, and water intake, and decreases in rectal temperature were observed after infection with *Streptococcus pneumoniae*. The survival rate was 0%.

In the 17-day administration group to which the lactic acid bacteria powder was administered both before and after *Streptococcus pneumoniae* inoculation (all-period administration group), the changes in feed intake and water intake were small, and the effects on general condition, rectal temperature, and body weight were milder than those in the control group. The survival rate was 60%, which was significantly higher than that of the control group.

In the 7-day administration (pre-inoculation administration) group to which the lactic acid bacteria powder was administered only for the period preceding the *Streptococcus pneumoniae* inoculation, the change in water intake was small, and the effects on general condition, rectal temperature, body weight, and feed intake were milder than those in the control group. The survival rate was 20%.

In the 10-day administration group which was administered the power starting at the day of *Streptococcus pneumoniae* inoculation (post-inoculation administration group), the effects on rectal temperature, feed intake, and water intake were milder than those in the control group, but the effects on general condition and body weight were comparable to those in the control group. The survival rate was 10%.

Collectively, the results indicate that the administration of lactic acid bacteria powder EF-2001, an ingredient of lactobacilli-containing beverages, is most effective in preventing infection if it is started before *Streptococcus pneumoniae* infection and is continued even after the infection. Of note, administration performed only before or after infection proved to exhibit preventive and therapeutic effects on infection although they are more limited than those observed in the all-period administration group.

The publications, patents, and patent applications mentioned herein are all incorporated herein by reference in their entirety.

INDUSTRIAL APPLICABILITY

The present invention is useful for preventing and/or treating *Streptococcus pneumoniae* infection.

The invention claimed is:

1. A method for treatment of *Streptococcus pneumoniae* infection, comprising orally administering to a subject a pharmaceutically effective amount of killed *Enterococcus faecalis*, strain EF-2001.

2. The method of claim 1, wherein the killed *Enterococcus faecalis* strain EF-2001 is orally administered in an amount of $1\times10^8$-$1\times10^{11}$ CFU/kg body weight per dose.

3. The method of claim 2, wherein the killed *Enterococcus faecalis* strain EF-2001 is orally administered one or more times per day in an amount of $1\times10^8$-$1\times10^{11}$ CFU/kg body weight per dose.

4. The method of claim 3, wherein the killed *Enterococcus faecalis* strain EF-2001 is orally administered one to five times per day in an amount of $1\times10^8$-$1\times10^{11}$ CFU/kg body weight per dose.

5. The method of claim 1, wherein the killed *Enterococcus faecalis* strain EF-2001 is orally administered in an amount of $1\times10^9$-$5\times10^{10}$ CFU/kg body weight per dose.

6. The method of claim 5, wherein the killed *Enterococcus faecalis* strain EF-2001 is orally administered one or more times per day in an amount of $1\times10^9$-$5\times10^{10}$ CFU/kg body weight per dose.

7. The method of claim 6, wherein the killed *Enterococcus faecalis* strain EF-2001 is orally administered one to five times per day in an amount of $1\times10^9$-$5\times10^{10}$ CFU/kg body weight per dose.

8. The method of claim 1, wherein the killed *Enterococcus faecalis* strain EF-2001 is orally administered in an amount of $1.2\times10^{10}$ or more CFU/kg body weight per dose.

9. The method of claim 8, wherein the killed *Enterococcus faecalis* strain EF-2001 is orally administered one or more times per day in an amount of $1.2\times10^{10}$ or more CFU/kg body weight per dose.

10. The method of claim 9, wherein the killed *Enterococcus faecalis* strain EF-2001 is orally administered one to five times per day in an amount of $1.2\times10^{10}$ or more CFU/kg body weight per dose.

11. The method of claim 1, wherein the killed *Enterococcus faecalis* strain EF-2001 is orally administered for seven or more days.

* * * * *